United States Patent
Anderson et al.

(10) Patent No.: US 12,285,210 B2
(45) Date of Patent: *Apr. 29, 2025

(54) METHOD AND APPARATUS FOR TISSUE EXPANSION

(71) Applicant: The General Hospital Corporation, Boston, MA (US)

(72) Inventors: Richard Rox Anderson, Boston, MA (US); Andrea Willey, Sacramento, CA (US); William A. Farinelli, Danvers, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/335,756

(22) Filed: Jun. 15, 2023

(65) Prior Publication Data
US 2024/0206969 A1    Jun. 27, 2024

Related U.S. Application Data

(60) Continuation of application No. 16/820,895, filed on Mar. 17, 2020, now Pat. No. 11,712,297, which is a
(Continued)

(51) Int. Cl.
*A61B 17/3209* (2006.01)
*A61B 17/322* (2006.01)
(Continued)

(52) U.S. Cl.
CPC ........ *A61B 18/20* (2013.01); *A61B 17/32093* (2013.01); *A61B 17/322* (2013.01);
(Continued)

(58) Field of Classification Search
CPC .......... A61B 17/3209; A61B 17/32093; A61B 2017/3225
See application file for complete search history.

(56) References Cited

U.S. PATENT DOCUMENTS

| 3,640,279 A | 2/1972 | Brown et al. |
| 5,004,468 A * | 4/1991 | Atkinson ............. A61B 17/322 606/132 |

(Continued)

OTHER PUBLICATIONS

PCT International Search Report and Written Opinion, PCT/US2009/039125, Nov. 16, 2009, 9 pages.
(Continued)

*Primary Examiner* — Ashley L Fishback
(74) *Attorney, Agent, or Firm* — QUARLES & BRADY LLP

(57) ABSTRACT

Exemplary embodiments of the present disclosure provide method and apparatus for facilitating stretching of a biological tissue by forming a plurality of micro-slits in the tissue. Each micro-slit can be less than about 2 mm or less than about 1.5 mm long, or even less than about 1 mm, such that small gaps that can heal quickly can be formed when the tissue is stretched. The micro-slits can be formed using a plurality of cutting arrangements or an ablative laser. The micro-slits can be formed in various patterns, including staggered rows, circular or spiral patterns, or random patterns.

20 Claims, 15 Drawing Sheets

Related U.S. Application Data division of application No. 15/677,935, filed on Aug. 15, 2017, now Pat. No. 10,624,698, which is a continuation of application No. 12/936,161, filed as application No. PCT/US2009/039125 on Apr. 1, 2009, now abandoned.

(60) Provisional application No. 61/041,591, filed on Apr. 1, 2008.

(51) Int. Cl.
*A61B 18/20* (2006.01)
*A61B 90/00* (2016.01)
*A61F 2/00* (2006.01)
*A61F 2/10* (2006.01)

(52) U.S. Cl.
CPC ............ *A61B 90/02* (2016.02); *A61F 2/0059* (2013.01); *A61F 2/105* (2013.01)

(56) References Cited

U.S. PATENT DOCUMENTS

| | | |
|---|---|---|
| 5,713,375 A | 2/1998 | McAllister |
| 5,810,857 A | 9/1998 | Mackool |
| 5,879,326 A | 3/1999 | Godshall et al. |
| 5,989,273 A | 11/1999 | Arnold |
| 6,063,094 A | 5/2000 | Rosenberg |
| 6,197,039 B1 | 3/2001 | Ashraf |
| 6,500,187 B1* | 12/2002 | Petersen ............ A61B 17/3213 30/329 |
| 6,537,264 B1 | 3/2003 | Cormier et al. |
| 6,881,203 B2 | 4/2005 | Delmore et al. |
| 6,887,250 B1 | 5/2005 | Dority et al. |
| 7,658,728 B2 | 2/2010 | Yuzhakov |
| 8,376,984 B2* | 2/2013 | James ................. A61B 17/205 604/46 |
| 2003/0181936 A1 | 9/2003 | Trautman et al. |
| 2004/0175690 A1 | 9/2004 | Mishra et al. |
| 2005/0283141 A1 | 12/2005 | Giovannoli |
| 2006/0271070 A1 | 11/2006 | Eriksson et al. |
| 2010/0057100 A1 | 3/2010 | Zeevi |

OTHER PUBLICATIONS

Brannon, Skin Anatomy, Skin Layers and Anatomy—Basic Overview, Jul. 30, 2004 (updated Dec. 19, 2014), https://web.archive.org/web/20150329121127/http://dermatology.about.com/cs/skinanatomy/a/anatomy.htm, 4 pages.

Dunkin et al., Scarring Occurs at a Critical Depth of Skin Injury: Precise Measurement in a Graduated Dermal Scratch in Human Volunteers, Plastic and Reconstructive Surgery, 2007, 119(6):1722-1732.

Salam et al., The Basic Z-Plasty, American Family Physician, 2003, 67(11):2329-2332.

* cited by examiner

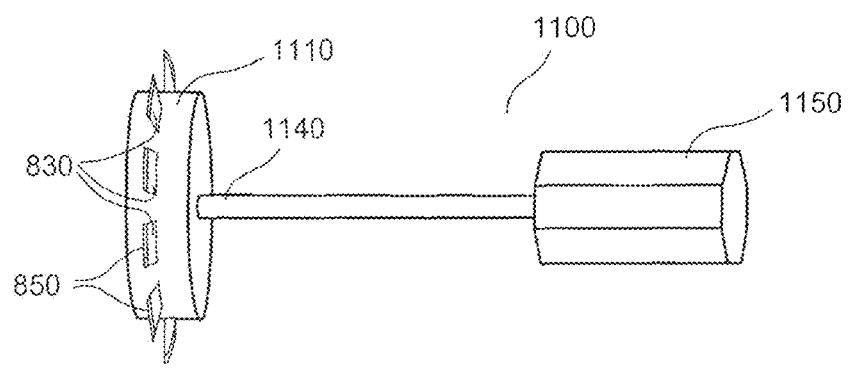
F I G. 11A
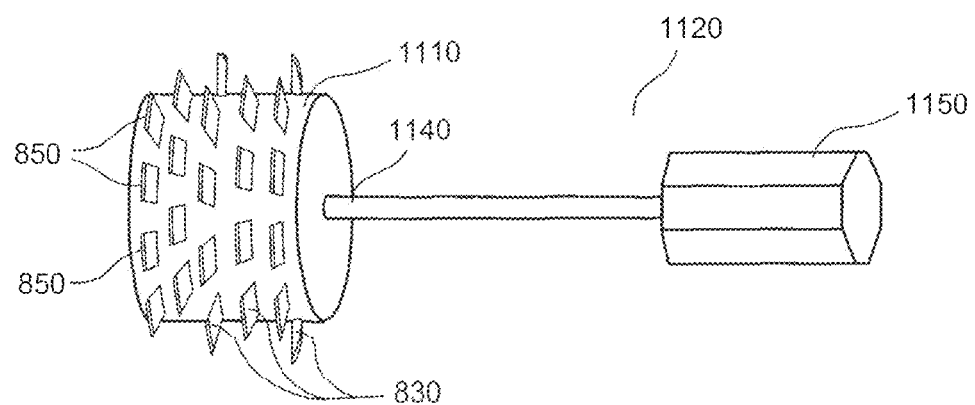
F I G. 11B

METHOD AND APPARATUS FOR TISSUE EXPANSION

CROSS REFERENCE TO RELATED APPLICATION

The present application is a continuation of U.S. patent application Ser. No. 16/820,895 filed Mar. 17, 2020, which is a divisional of U.S. patent application Ser. No. 15/677,935 filed Aug. 15, 2017, now U.S. Pat. No. 10,624,698, which is a continuation of U.S. patent application Ser. No. 12/936,161 filed on May 20, 2012, which claims priority from International Patent Application No. PCT/US2009/039125 filed Apr. 1, 2009, and from U.S. Provisional Patent Application Ser. No. 61/041,591 filed Apr. 1, 2008, the disclosures of which are incorporated herein by reference in their entireties.

FIELD OF THE DISCLOSURE

The present disclosure relates to an expansion of biological tissue, and in particular to exemplary embodiments of method and apparatus which can provide such expansion.

BACKGROUND INFORMATION

Expansion of connective tissue, especially skin, fascia, cartilage and tendon, is often desirable for cosmetic or functional purposes. Achieving tissue expansion without damaging, impairing, or aesthetically harming the tissue is a common concern in reconstruction after surgery, trauma, and for various medical and congenital disorders. Tissue expansion can be used for tension relief of contracted surgical, traumatic, and burn scars. For example, burn victims often suffer through many painful surgeries performed to relieve the tension and contraction of hypertrophic scars. After excision of skin cancer on the forehead and scalp, large defects are often left to heal openly because the surrounding skin cannot be moved enough to close the wound. On the legs, skin healing can be poor and the skin is relatively inelastic, such that surgical wounds and ulcers on the legs are difficult to close. Scalp reduction surgery can be limited by the rigidity of scalp skin. In addition to a need for tissue stretching of skin in these examples, tissue stretching can also be useful for lengthening tendons, re-shaping cartilage, and for expanding other connective tissues.

Conventional techniques for stretching tissue include, e.g., (a) subcutaneous implantation of saline-filled balloons to expand the skin prior to surgery, (b) using incisions to create various artful flaps that move skin from one location to another without removing it entirely, such that tension is relieved and/or missing tissue is replaced by mobilizing the surrounding tissue, and (c) tissue grafts, which involve removal of skin or other connective tissue from one location and placing it on another location. Tissue grafts can be used to replace skin or other tissue that has been removed by surgery or trauma. For example, split-thickness skin grafts can be used to cover a wound in burn and skin ulcer patients. A conventional split-thickness graft can be made, e.g., by harvesting a sheet of epidermis and upper dermis tissue from a donor site, much like peeling an apple, which can then be placed on the burn or ulcer location. The skin tissue can then grow back on the donor site following a generally extended healing time.

Split thickness grafts may often be "meshed" for expansion, so they can cover a larger area than the donor site. Conventional tissue meshing includes formation of an array of many slits, typically several millimeters in length or longer, which can open into diamond-shaped or lens-shaped holes when the meshed graft is subjected to tension and expanded. These holes can facilitate an overall expansion of the graft. The expanded meshed tissue sheet generally may have an appearance of a chain-link fence, with large holes that can remain visible after the graft is placed and the tissue is healed. Thus, meshed grafts may save a burn victim's life by expanding the usable area of skin available from donor sites, but they also can contribute to life-long aesthetic disfigurement.

Conventional full-thickness grafts generally include a removal of epidermal tissue and the complete thickness of the dermis from a donor site to be used as a graft, with the edges of skin adjacent to the removed tissue being re-opposed at the donor site. Meshing may not be ideal for expanding full-thickness grafts because, for example, (a) the lens-shaped holes left by gross meshing and expansion of full-thickness skin can be even more disfiguring than in split-thickness grafts because they are much deeper, and may look like an array of acne scars after healing, and (b) the large, full-thickness holes can take weeks to heal because cells from the surrounding dermis have to build new fibrotic tissue to fill in the substantial volume of each hole. Similarly, meshing of flaps may not be appropriate because skin incisions within a flap can sever some of the blood supply to the flap, thus impairing the viability of the flap tissue. For these reasons, conventional tissue meshing may generally not be suitable for expansion of skin grafts or flaps during surgery, and not for relief of tension on scars, nor to modify the scar tissue itself.

Accordingly, there can be a need to address and/or overcome at least some of the deficiencies or issues described herein above.

SUMMARY OF EXEMPLARY EMBODIMENTS

Embodiments of the present disclosure are directed to method and apparatus for facilitating an expansion of a portion of tissue, while reducing a presence or likelihood of noticeable holes or scars after healing of the expanded tissue. The exemplary method and apparatus can be applied in situ for releasing local skin tension, to cover damaged or removed regions of tissue using adjacent healthy tissue, and other tissue expansion applications, or ex vivo for expansion of split-thickness and/or full thickness grafts while providing an improved outcome.

According to one exemplary embodiment of the present disclosure, a method can be provided for facilitating tissue expansion that includes a formation of a plurality of micro-slits in the tissue to be stretched. The length of extension of the micro-slits can be less than about 2 mm, or less than about 1.5 mm, or less than about 1 mm, or even less than about 0.8 mm. The length of each micro-slit can be greater than about 0.1 mm to allow sufficient expansion of the tissue. The width of the gap formed by a micro-slit when the tissue is expanded can be less than about 1 mm, or preferably less than about 0.5 mm.

Such micro-slits may extend through an entire depth of the tissue (e.g., in a full-thickness graft or a split-thickness graft), or to a particular depth such as, e.g., the depth of the dermis (e.g., for in situ meshing and stretching). A force can then be applied to the tissue to expand it, which can widen the micro-slits to form lens-shaped or rounded gaps therefrom. The small dimensions of the micro-slits—and the gaps formed therefrom after stretching—can facilitate rapid regrowth and filling of these gaps, which can be facilitated by adjacent functional tissue. A shallower depth can also be formed, e.g., a depth of about 0.6 mm in skin tissue, or about one-third (⅓) of the skin thickness, which can assist in avoiding formation of scars after the tissue is stretched and allowed to heal. Accordingly, the use of such micro-slits can reduce healing times and result in an aesthetically pleasing appearance of the stretched tissue.

In certain exemplary embodiments of the present disclosure, micro-slits can be provided in a form of z-shaped incisions, such that triangular flaps formed by these incisions can be repositioned to allow expansion of the tissue with little or no gap being formed.

For example, micro-slits can be formed in a pattern of alternating lines of staggered micro-slits, where the gap between adjacent micro-slits in a line can be greater than about one-tenth (¹⁄₁₀th) of the length of an adjacent micro-slit, and where the spacing between adjacent lines of micro-slits can be between about ⅓ and 3 times the length of a micro-slit. Micro-slits can also be provided in other patterns, such as random arrays, circular or spiral patterns, or arrays containing orthogonal lines of micro-slits. According to another exemplary embodiment of the present disclosure, an apparatus can be provided which is configured to form micro-slits in a tissue. The exemplary apparatus can include one or more blades, where each blade can further include one or more extensions or protrusions, with each having a sharp cutting edge. For example, the width of the extensions can correspond to the approximate width of the micro-slits formed when each extension is pressed into the tissue.

In yet another exemplary embodiment, the apparatus can include a stack of such blades that can be spaced apart from one another by a particular distance, e.g., using spacer elements between the blades. Such exemplary apparatus can be used to form a plurality of micro-slits simultaneously using a 'stamping' procedure, whereby the ends of the blades having sharp cutting edges are pressed into the tissue and then withdrawn. This exemplary stamping procedure can be repeated in different locations on the tissue to provide micro-slit meshing for a larger tissue area.

In a further exemplary embodiment of the present disclosure, a roller apparatus can be provided that includes a plurality of extensions provided on one or more circular blades, where the circular blades are configured to rotate around an axle in a roller configuration. The exemplary roller apparatus can optionally include a handle coupled to the axle. The circular blades can be rolled over the tissue, and the extensions around the perimeter of the circular blades penetrate the tissue to form a plurality of micro-slits.

According to still another exemplary embodiment of the present disclosure, an apparatus can be provided which is configured to form micro-lines in tissue using optical energy such as, e.g., an ablative laser apparatus. The exemplary apparatus can include, for example, a laser source, a controller, and an optical arrangement. The laser source can be an ablative laser such as a CO2 laser or the like. The controller circuitry can be configured to control parameters of the laser source and of the optical arrangement, for example, to form a plurality of micro-slits in the tissue by direct energy from the laser source to ablate thin regions of the tissue to a particular depth. According to yet another exemplary embodiment of the present disclosure, an apparatus for facilitating an expansion of a biological tissue can be provided. In particular, a plurality of cutting arrangements can be provided, with each cutting arrangement comprising at least one cutting edge structured to cut at least one respective micro-slit in the tissue. For example, a length of extension of the cutting edge(s) of at least one of the cutting arrangements can be less than about 2 mm or less than about 1.5 mm (or possibly less than about 1 mm or 0.8 mm). In addition, each of the cutting edge(s) of each of the cutting arrangements can comprises a plurality of cutting edges that have a length of extension that is less than about 2 mm or less than about 1.5 mm (or possibly less than about 1 mm or 0.8 mm).

According to another embodiment, a method for forming micro-slits in a tissue is provided. The method includes applying to the tissue: a roller apparatus coupled to an axle and a plurality of extensions adapted to protrude so that, when the apparatus is rolled over the tissue, the extensions can penetrate the tissue and simultaneously generate one or more lines of micro-slits in the tissue.

These and other objects, features and advantages of the present disclosure will become apparent upon reading the following detailed description of exemplary embodiments of the invention, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which:

FIG. 11A is an illustration of a first exemplary roller apparatus that can be used to form the micro-slits;

FIG. 11B is an illustration of a second exemplary roller apparatus that can be used to form the micro-slits;

Figure 1A:
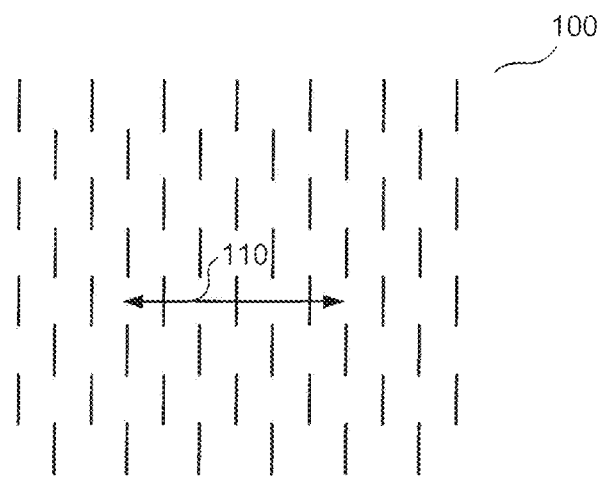
FIG. 1A is an illustration of a first exemplary pattern of micro-slits that can be used to expand tissue in accordance with the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

Exemplary embodiments of the present disclosure provide method and apparatus for facilitating tissue expansion by forming a plurality of micro-slits in the tissue, where each micro-slit is sufficiently small such that it may not be easily seen by the human eye without magnification. By providing a plurality of such small micro-slits in a tissue, it is possible to utilize a procedure that can be referred to as "micro-meshing," such that the gross appearance of the tissue (e.g., skin) when expanded may remain substantially normal after healing. Accordingly, such exemplary micro-meshing procedure can be used in situ, for example, in place of other conventional techniques, such as advancement flaps or skin tension release operations, which can be more problematic. Exemplary embodiments of the present disclosure can also provide ways to eliminate a need for a tissue graft in certain applications by facilitating a stretching of adjacent tissue in situ that can exhibit a substantially normal appearance after healing.

According to a first exemplary embodiment of the present disclosure, a method can be provided for facilitating tissue stretching by forming a plurality of micro-slits in full or partial thickness tissue such as, e.g., skin or other connective tissue. The size, orientation, density, and configuration of the micro-slits can be selected to facilitate a certain amount of tissue expansion for a particular application as described herein. Such micromesh tissue expansion can be accomplished in situ, e.g. by providing micro-slits in skin tissues adjacent to or at some distance from a local wound that needs to be closed, to facilitate stretching of the skin tissue over the wound. Such exemplary method can also be used, e.g., to facilitate the expansion of graft tissues, such as a piece of skin harvested from a donor site that can be used to cover a wound.

Figure 1B:
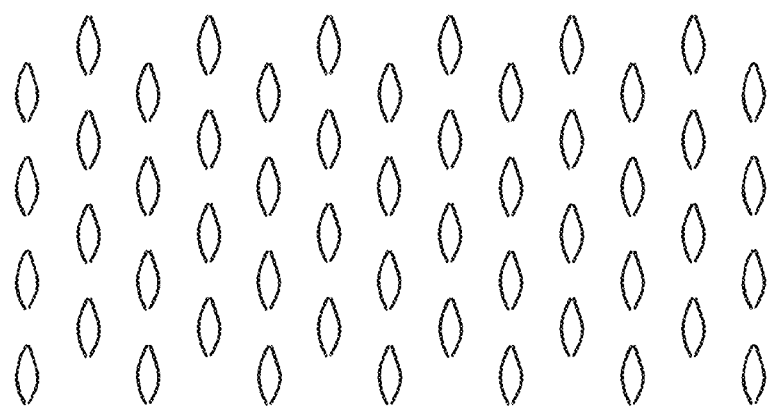
FIG. 1B shows an illustration of the pattern of the micro-slits of FIG. 1A after the tissue has been expanded to form a plurality of small gaps in the tissue.

An exemplary array 100 of micro-slits is shown in FIG. 1A. This exemplary micro-slit array 100 has a form of staggered rows of collinear slits. Such array can be used, e.g., to facilitate a substantially unidirectional expansion of the tissue in the direction of arrow 110. FIG. 1B illustrates the exemplary array 100 after it has been stretched. Each micro-slit has widened to form a small lens-shaped gap that facilitates the overall tissue length to increase in the direction of the arrow 110 without significant contraction in the perpendicular direction along the tissue surface. These small gaps may rapidly fill in with the regrown tissue as the stretched tissue heals.

For example, the length of the micro-slits can be less than about 2 mm, or less than about 1.5 mm, to avoid a likelihood of forming visible scars and/or to allow a rapid regrowth of the gaps formed in the expanded micro-slits. The length of the micro-slits can be less than about 1 mm, or less than about 0.8 mm. The length of each micro-slit can be greater than about 0.1 mm to facilitate a sufficient expansion of the tissue using a reasonable number of slits. In general, a maximum width of the gap formed by each micro-slit when the tissue is expanded is preferably less than about 1.5 mm. This width of the gaps can also be less than about 1.0 mm, or less than about 0.5 mm.

Small micro-slits as described herein can provide several advantages over conventional meshing techniques. For example, each of the micro-slits can be a tissue wound that forms a gap when the tissue is expanded. This gap may eventually be filled in by a wound healing process. Clinical experience indicates that very small wounds may heal by regrowth of healthy tissue, a process that can be referred to as remodeling, with little or no scar tissue formation. During tissue remodeling, local structures such as hair follicles, sebaceous and sweat glands are capable of local regeneration when injured on the scale of the structure itself, e.g., at distances of less than about 1 mm. Examples of tissue injury that can be healed by remodeling include, e.g., tattoo placement (which may involve a healing of thousands of microscopic puncture wounds), and healing of single puncture wounds created by insertion of hypodermic needles or the like.

In contrast, large wounds may heal by replacement of damaged or lost tissue with undesirable scar tissue. Scar tissue can re-establish physical integrity, but it often can be dysfunctional. In skin, scar tissue lacks hair follicles, sweat glands, and normal dermal and dermo-epidermal junction structure. Scar tissue can also be mechanically stiff as compared with healthy tissue. Over time, scars subjected to tension may react by contraction. This response can be observed after burn trauma and surgery, and can be debilitating. Accordingly, using micro-slits having a size smaller than that used in conventional tissue meshing, e.g., less than about 2 mm or less than about 1.5 mm in length, can facilitate a prevention of a formation of significant amounts of scar tissue after the stretched tissue heals. Further, generating micro-slits having a length that is smaller than that of a diameter or typical spacing of major skin arteries can facilitate a meshing of the tissue that may not fully or substantially sever its blood supply. Healing of the gaps created in the expanded tissue after micro-meshing can also occur more rapidly than healing of larger gaps created using conventional meshing techniques, because of the smaller distances and areas of regrowth that occur, supported by adjacent healthy tissue.

Using a small micro-slit size for tissue expansion, especially in skin, can provide further advantages, e.g., in the appearance of the tissue after expansion and healing. Even if a small amount of scar tissue forms in each micro-mesh incision, a grossly visible scar can be avoided. Such micro-slits can create small "dells" in the skin surface after healing that can effectively disappear among normal dermatoglyphics (e.g., permanent skin surface texture features). An ability to visually resolve a skin feature can depend on a size of the feature, and a distance from which it is viewed. The micro-meshing procedure performed in accordance with the exemplary embodiments of the present disclosure can be performed using a plurality of micro-slits, each of which can be approximately at or below the resolution of human vision under typical viewing conditions, e.g., from a distance of about 0.5 meter.

As an example of this visual effect, newsprint photographs can be composed using individual ink spots having feature sizes that are below the resolution limit of the naked eye when viewed at typical distances. Such photographs can be formed, for example, using small dots of ink spaced about 0.5 mm apart in a simple array. Although all points on the photograph can be either white (e.g., spaces between ink dots) or black (e.g., points within an ink dot), the photograph may appear as a full gray-scale range to the naked eye because the ink dots are not individually resolved. The size of each ink dot can be varied from zero to completely intersecting with its neighbors, which can produce white and black regions, respectively. A full gray scale can be obtained for portions of the array containing intermediate-sized dots.

An appearance of such newsprint photographs as apparently continuously varying shades of gray can be analogous to skin appearance after micro-meshing, in which a uniform appearance can be obtained despite the presence of very small regions of the regrown tissue. An exemplary size range for micro-slits cut into tissue to facilitate tissue expansion can be somewhat greater than that for typical newsprint photographs, because there can be a lower contrast between the original and the regrown tissue as compared to the contrast between the white paper and black ink dots.

Using small micro-slit and gap sizes as described herein for tissue expansion facilitated by the exemplary micro-meshing procedure can also facilitate rapid healing after the tissue is stretched. The healing time for a gap in the tissue can be approximately proportional to the size of the gap. For example, during fractional laser ablative resurfacing of skin, a large number of small holes (e.g., each hole being about 0.2 mm diameter and 2 mm deep) can be produced, removing up to about 50% of the skin tissue. Within several days the epidermis can cover each hole, and within a week the holes can be filled in by remodeling without scarring. Similar rapid healing can be obtained in tissue stretching by forming a plurality of micro-slits in the tissue, such that the size of the gap formed by each micro-slit after stretching remains small.

The depth of the micro-slits can be sufficiently large to pass through an entire thickness of a tissue graft (e.g., for an ex vivo tissue sample) or the tissue layer or structure (e.g., for in situ applications) to be expanded. For example, split-thickness skin grafts can typically be about 0.2 mm thick, and micro-slits used for expanding such grafts can be sufficiently deep to pass entirely through this thickness. The micro-slits can also be formed in full-thickness grafts, e.g., that pass through the entire thickness of such grafts. The micro-slits having a shallower depth can also be formed. For example, the micro-slits can be formed that have a depth of less than about 0.6 mm in skin tissue, or less than about ⅓ of the total skin thickness. The micro-slits having such depths can facilitate healing of the tissue after such tissue is stretched while avoiding significant scar formation as described, e.g., in Plastic Reconstructive Surgery, vol. 119, pp. 1722-32 (2007).

Micro-mesh expansion of other connective tissue such as tendon, ear cartilage, etc., can be done using various micro-slit depths that can be selected based on mechanical properties of the tissue and the amount of stretching desired. Tissue expansion can also be accomplished in three dimensions for organ tissues such as kidney, heart, and liver by forming appropriate micro-slits in various orientations, e.g., in at least one of the xy, yz, and/or xz planes. The exemplary micro-slit array 100 shown in FIG. 1A can be used to facilitate tissue expansion that can be substantially unidirectional. The exemplary array 100 can be provided as a plurality of substantially parallel dashed lines, where each dash can represent a micro-slit formed in the tissue. The micro-slits can be in a staggered alignment, such as that shown in FIG. 1A, which may facilitate a substantially uniform unidirectional expansion of the tissue when an appropriate force is applied, as shown in FIG. 1B. Some staggering or offset of the micro-slits in some rows of slits, e.g., in adjacent rows, can be provided such that any imaginary line drawn across the tissue substantially in the direction of expansion 110 can intersect a plurality of micro-slits that can widen by forming gaps in a direction substantially parallel to the arrows. Such staggering or offset of slit lines can thereby help to avoid formation of continuous regions of un-slit tissue along the elongation direction, where such regions would lack gap-forming slits to accommodate the overall expansion and thereby can be undesirably strained.

Figure 2:
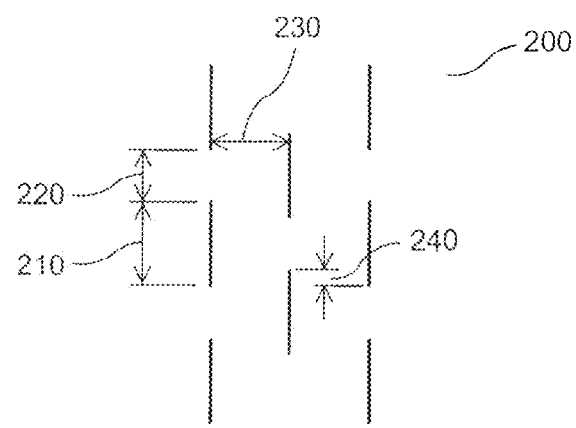
FIG. 2 is an illustration of a portion of the micro-slit pattern shown in FIG. 1A.

A portion 200 of the exemplary micro-slit array 100 is shown in FIG. 2. Parameters which can be used to describe the exemplary micro-slit array include, e.g., a micro-slit length 210, a gap length between adjacent micro-slits 220, a spacing 230 between adjacent lines of micro-slits, and an overlap 240 between neighboring micro-slits in adjacent rows. The gap length 220 can be at least about ⅒ of the micro-slit length 210. This exemplary ratio can provide sufficient tissue between adjacent micro-slits to maintain integrity of the tissue when it is stretched. The spacing 230 between adjacent lines of micro-slits can be between about ⅓ and 3 times the length of the adjacent micro-slits. Spacings 230 that are smaller than this ratio range can reduce the mechanical integrity of the tissue when stretched, and spacings larger than this ratio range may not facilitate a sufficient expansion of the tissue.

The overlap 240 between neighboring micro-slits in adjacent rows can be between about ⅒ and ⅘ of the length of adjacent micro-slits. The larger overlap can provide a gap length 220 of at least about ⅒th of the adjacent micro-slit length 210 to be maintained between adjacent micro-slits in a line. An overlap 240 of, e.g., at least ⅒th of the adjacent micro-slit length 210 can be effectuated so that there are no extended regions of tissue in the direction of the tissue expansion that are free of any expandable micro-slits. Such extended micro-slit-free regions, if present, can be subjected to excessive strains and possibly tear because there are no micro-slits available locally to form gaps and accommodate the overall tissue expansion.

In addition to the exemplary micro-slit array 100 shown in FIG. 1A, which can provide unidirectional expansion of tissue, other slit arrangements can be provided to facilitate various expansion behaviors while maintaining small micro-slit and gap sizes as described herein. For example, micro-slit configurations similar to the array 100 shown in FIG. 1A can be used, where the slit lengths, the spacing between adjacent lines, and/or the spacing between slits in a single line can be varied. Generally, a portion of tissue having closely-spaced lines of micro-slits can be stretched more than a portion having similar lines of slits spaced further apart. Line spacings can thus be varied in such an array to provide portions of tissue that can be stretched to varying degrees within a single graft or skin region. Certain further portions of the tissue being stretched can also be free of any micro-slits to inhibit stretching in these portions. Such variations in a local expandability can be used to provide improved cosmetic appearance of the stretched tissue or applied graft, e.g., based on such factors as hair follicle density, pigmentation, etc.

Figure 3:
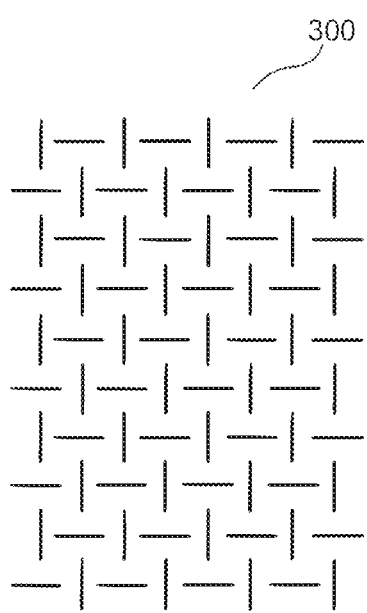
FIG. 3 is an illustration of a second exemplary pattern of the micro-slits that can be used to facilitate the tissue expansion.

Exemplary embodiments of the present disclosure can also facilitate for a use of tissue having an exemplary configuration or array of micro-slits 300 such as that shown in FIG. 3, which includes intersecting lines of micro-slits that lie substantially along one of two substantially orthogonal directions. Such array of slits 300 can be capable of facilitating expansion of the tissue in any direction. For example, an arbitrary direction for stretching can generally be expressed as a vector combination of two orthogonal stretching components that can be perpendicular to the two orthogonal slit directions. Stretching of the tissue in a direction orthogonal to each line of micro-slits can be accommodated by facilitating the micro-slits to form gaps in that direction as shown in the exemplary embodiment of FIGS. 1A and 1B. Thus, regular micro-slit arrays, such as the exemplary array 300 shown in FIG. 3, can be used to provide grafts or regions of in situ tissue that can be more easily expanded in any direction.

Figure 18A:
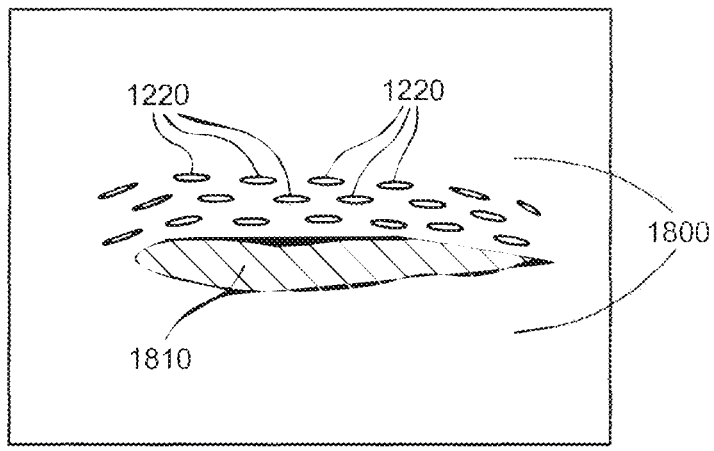
FIG. 18A is an illustration of an exemplary pattern of the micro-slits that can be used to expand tissue in situ in accordance with the present disclosure.
Figure 18B:
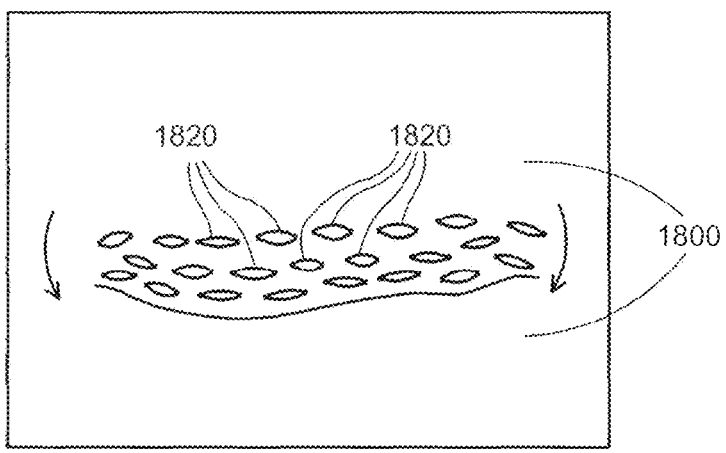
FIG. 18B is an illustration of the in situ tissue shown in FIG. 18A after such tissue has been stretched.

The exemplary micro-slits described herein can also be used to stretch skin in situ, e.g., to cover certain wounds or damaged skin regions with tissue from adjacent healthy regions. An exemplary illustration of such in situ stretching procedure is shown in FIGS. 18A and 18B. For example, a plurality of micro-slits 1220 can be formed in a healthy tissue 1800 that is adjacent or proximal to a wound 1810. For example, the wound 1810 can be a portion of the tissue where an outer layer of the skin is missing, e.g., a portion of the skin surface that may have been burned or abraded. The wound 1810 can be cleaned to remove any remaining portions of the damaged tissue and/or to provide a uniform and sterile base of tissue capable of receiving an overlayer of stretched tissue.

The exemplary micro-slits 1220 shown in FIG. 18A can be formed such that a surface direction of the micro-slits 1220 is substantially perpendicular to the direction that the healthy tissue 1800 is to be stretched. A local density of the micro-slits 1220 can also be higher in regions of the healthy tissue 1800 that is to be stretched further, e.g., those regions that are to undergo a greater areal expansion to cover the wound 1810. FIG. 18B shows an exemplary illustration of the healthy tissue 1800 shown in FIG. 18A after such tissue has been stretched to cover the wound 1810. The micro-slits 1220 can be formed as described herein, and can be provided in a sufficient density that a gap 1820 formed by each stretched micro-slit is small, e.g., less than about 1.5 mm in width, or less than about 1 mm in width. Such small gaps 1820 can facilitate a rapid healing of the stretched tissue 1800, and can avoid a formation of visible scars.

The healthy skin tissue 1800 can be about 1-3 mm thick. The micro-slits 1220 that are formed to facilitate the expansion of this skin tissue 1800 in situ can be provided at least to a depth so as to extend through substantially the entire local dermal layer. For example, the dermal layer of the skin 1800 may not be strongly attached to the fatty layer below, such that the skin 1800 can more easily separate from the underlying fatty layer, and be stretched to widen the gaps 1820 in the micro-slits 1220. The micro-slits 1220 formed in situ may, e.g., not extend into the underlying tissue below the dermis to any significant depth, to avoid damaging blood vessels and/or other structures underlying the skin tissue 1800.

Figure 4:
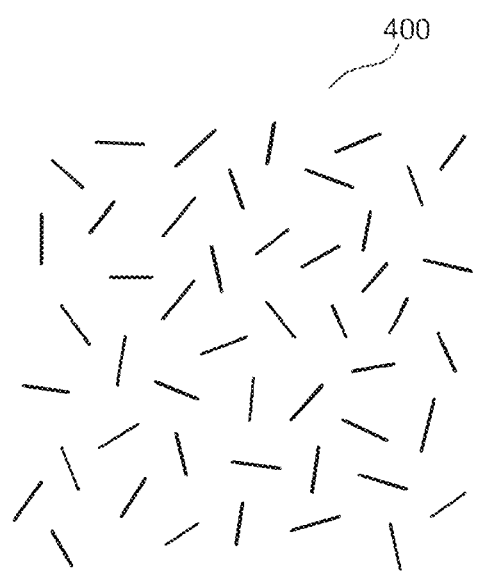
FIG. 4 is an illustration of a third exemplary pattern of the micro-slits that can be used to facilitate the tissue expansion.

In further exemplary embodiments, micro-slit arrays can be formed using micro-slits oriented in a plurality of directions, such as in the exemplary micro-slit array 400 shown in FIG. 4. The micro-slits can be formed in a pattern which may repeat at some distance, or their positions and/or orientations can be random. The exemplary array 400 shown in FIG. 4 can be used to facilitate the expansion of portions of the tissue in different directions. The micro-slits can be provided in a substantially non-intersecting pattern to reduce or avoid a formation of wide gaps and/or pointed flaps of tissue after expansion is achieved by applying appropriate tension to the micro-meshed tissue.

Figure 5A:
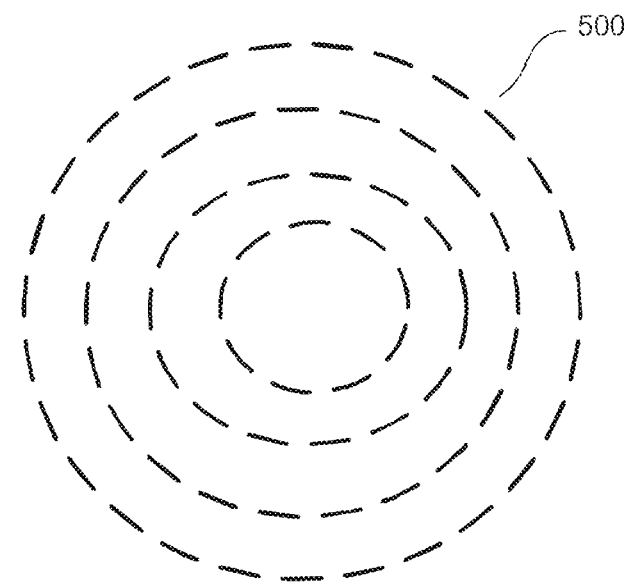
FIG. 5A is an illustration of a fourth exemplary pattern of the micro-slits that can be used to facilitate tissue expansion.
Figure 5B:
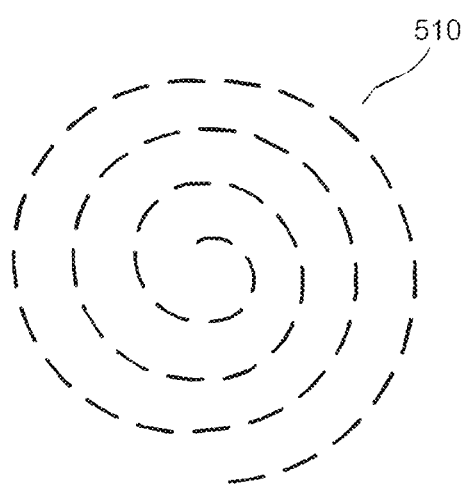
FIG. 5B illustrates a fifth exemplary pattern of the micro-slits that can be used to facilitate the tissue expansion.

In still further exemplary embodiments, a circular micro-slit pattern such as an exemplary pattern 500 shown in FIG. 5A can be used to facilitate a particular expansion behavior of the tissue. The round slit pattern shown in FIG. 5A can be used, for example, to facilitate the expansion of a nominally flat piece of tissue over a rounded surface such as, e.g., a chin or a shoulder. A micro-slit pattern that includes one or more spiral-shaped lines of slits, such as the exemplary pattern 510 shown in FIG. 5B, can also be used to facilitate a similar tissue expansion geometry.

Several exemplary parameters associated with the micro-slit arrays can be varied for particular applications including, for example, average micro-slit length, variation of micro-slit lengths, slit density (e.g., number of micro-slits per unit area of tissue), micro-slit orientations, spacing between micro-slits or lines of micro-slits (which can be related to the overall micro-slit density), and/or randomness of micro-slit staggering. A mean orientation of a group or pattern of the micro-slits can be selected to better facilitate tissue expansion in one or more particular directions. For example, if an expansion of the tissue is desired along a given vector, e.g., a primarily one-dimensional expansion, most or all of the micro-slits can be oriented substantially perpendicular to that vector, as shown in FIG. 1. An omnidirectional tissue expansion can be facilitated, e.g., by providing a plurality of micro-slits having a mean orientation vector that is nearly zero, e.g., as shown in FIGS. 3 and 4.

Figure 6A:
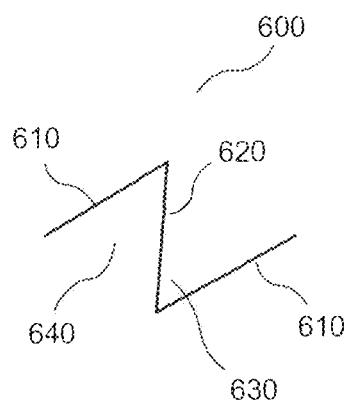
FIG. 6A is an illustration of an exemplary z-shaped micro-incision that can be used to facilitate the tissue expansion.

In further exemplary embodiments of the present disclosure, micro-slits can be provided to form a plurality of z-shaped micro-incisions 600, such as that shown in FIG. 6A. Such z-shaped micro-incisions can be similar in shape to incisions used, e.g., in a conventional z-plasty procedure as described, e.g., in Salam et al., American Family Physician, vol. 67, no. 11 (Jun. 1, 2003), pp. 2329-2332. The exemplary z-shaped micro-incisions 600 can include, e.g., two opposing micro-slits 610, which can be substantially parallel or at some small angle relative to each other, and a diagonal micro-slit 620 connecting near ends of the opposing micro-slits 610 to form two triangular flaps 630, 640.

Figure 6B:
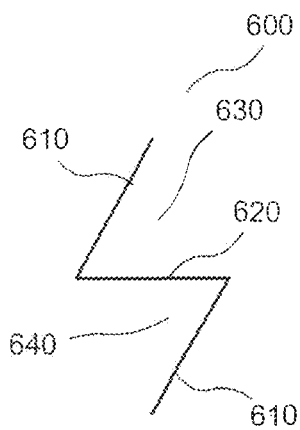
FIG. 6B shows an illustration of the exemplary z-shaped micro-incision of FIG. 6A after two triangular flaps have been transposed to provide a net lengthening of the tissue in a particular direction.

The relative positions of the flaps 630, 640 can be switched across the diagonal micro-slit 620, e.g., as shown in FIG. 6B, which can facilitate a net expansion of the tissue in the direction 650 and a slight contraction of the tissue in a direction substantially orthogonal to such direction 650. The micro-slits 610, 620 can be approximately the same length to facilitate the alignment of the flaps 630, 640 after they are repositioned as shown in FIG. 6B. Further, similar to conventional z-plasty procedures, the diagonal micro-slit 620 may intersect each of the two micro-slits 610 at substantially the same angle, which can also facilitate the alignment of the flaps 630, 640 when they are repositioned. This angle of intersection can be about 60 degrees or less, to avoid excessive local deformation of the tissue and to facilitate repositioning of the flaps 630, 640. Smaller angles can also be used, and they may provide a smaller amount of expansion when the flaps 630, 640 are repositioned.

Figure 7A:
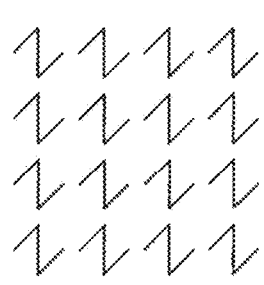
FIG. 7A is an illustration of a first exemplary array of z-shaped incisions that can be used to facilitate tissue expansion.
Figure 7B:
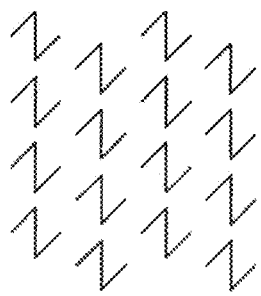
FIG. 7B is an illustration of a second exemplary array of z-shaped incisions that can be used to facilitate the tissue expansion.
Figure 7C:
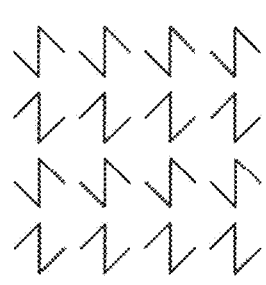
FIG. 7C is an illustration of a third exemplary array of z-shaped incisions that can be used to facilitate the tissue expansion.

A plurality of such z-shaped micro-incisions 600 can be provided in various arrays, such as the exemplary arrays shown in FIGS. 7A-7C. The size, orientation and/or spacing of the z-shaped micro-incisions 600 can be varied to provide different local expansion behavior of the tissue. Each of the micro-slits 610, 620 can be less than about 2 mm in length, or optionally less than about 1 mm. These micro-slit lengths of the z-shaped micro-incisions can be larger than corresponding lengths of single micro-slits, such as those shown in FIG. 1A. This is because much of the effective tissue expansion can be accomplished geometrically with a z-shaped micro-incision, such that smaller gaps can be formed when the tissue is stretched.

The micro-slit lengths described herein can be smaller than typical slit sizes used in conventional z-plasty techniques, and they can provide several advantages. For example, using the micro-slits 610, 620 to form a small z-shaped micro-incision 600 can facilitate the repositioning of the flaps 630, 640 when applying a local tension to the tissue containing the micro-slits 610, 620. The flaps 630, 640 are likely smaller relative to their thickness than larger conventional flaps, and therefore they can be comparatively rigid and easier to reposition properly.

The flaps 630, 640 can also be repositioned with little or no undermining of the tissue beneath them. In contrast, conventional z-plasty techniques can require significant undermining of tissue beneath the relatively large triangular flaps to provide them with sufficient mobility to be moved with respect to adjacent tissue and be repositioned. Further, the small z-shaped micro-incisions 600 can produce relatively small markings of the tissue after the tissue is expanded and healed that may not be apparent to the naked eye, and thereby likely avoid a formation of larger, more visible scars or tissue discontinuities. The flaps 630, 640 formed by the micro-slits 610, 620 can also avoid the use of stitches to hold them m place after repositioning, in contrast to some large flaps used in conventional z-plasty procedures. In addition, the alignment of the flaps 630, 640 does not have to be precise to obtain tissue expansion without formation of undesirable scars. For example, any gaps formed by the micro-slits 610, 620 after the tissue expansion can also be small (for example, less than about 0.5 mm). As described herein, functional tissue can preferentially regrow in such small gaps rather than scar tissue.

A general pattern of slits can produce the same relative expansion (expressed as a percentage or fraction of the original tissue lengths) at any size scale based on geometric similarity. For example, a particular array of large slits may provide approximately a 30% expansion in a certain direction by formation of lens-shaped gaps. If the size and spacings of the slits in the particular array are uniformly decreased by half (e.g., by 50%), the resulting array can also produce a 30% expansion by forming lens-shaped gaps having a similar shape. In this example, four times as many of the smaller slits can be provided per unit area (as compared with the large slits) to obtain this exemplary 30% expansion in a particular portion of tissue. The larger number of smaller slits is based on the 50% reduction in size scale, which doubles the number of slits per unit distance in each of two orthogonal directions parallel to the tissue surface. These particular exemplary percentages merely illustrate the effect of changing the size scale of a slit pattern. In general, miniaturizing a given pattern of mesh slits can provide substantially the same degree of tissue expansion as a larger slit pattern when forming gaps from the slits which have a geometrically similar shape.

Reducing the size scale of a slit pattern also proportionally can reduce the physical width of the gaps formed by the slits for a particular amount of overall tissue expansion. Thus, by using a pattern of micro-slits to expand tissue as described herein, the width of each gap formed when the tissue is expanded can be small. In general, the gap width used in tissue expansion can be less than about half the micro-slit length, or less than about one-quarter of the micro-slit length. Larger gap widths can also be used. For example, greater expansion can be achieved using a particular micro-slit pattern if the gap width approaches the length of the micro-slits. This can lead to formation of gaps that are more equiaxed in shape. Such wider gaps can also be useful for tissue expansion, particularly if the micro-slit length and gap width are small enough to allow tissue to regrow and fill in the gap without producing significant amounts of scarring or nonfunctional tissue.

In general, reducing the micro-slit size (or an average micro-slit size in an array or pattern of micro-slits having different sizes) can reduce the size of the gaps formed when the tissue is expanded. The micro-slits can be larger than some minimum size that are selectable, e.g., based on the type of tissue, the thickness of the tissue layer being expanded, the ease of forming small micro-slits, etc. The micro-slits can extend through substantially the entire thickness of the tissue being expanded. This can lead to larger aspect ratios of depth to length if very short micro-slits are formed in relatively thick tissue layers. Such narrow, deep micro-slits may not readily facilitate the uniform tissue expansion because of possible non-uniformities in the depth direction. Accordingly, a length-to-depth ratio of a micro-slit can be greater than about 1:10, or possibly greater than about 1:5. Length-to-depth ratios of about 1:2 can also be used, as can larger ratios.

Visible disfigurement associated with scars can result from a lack of dermatoglyphics, e.g., the scar tissue can have a smooth, often glossy surface. A pattern or array of micro-slits as described herein can be formed on a visible scar to disrupt the surface texture of the scar after healing, which can result in a dermatoglyphic appearance that is more similar to that of normal skin.

In another exemplary embodiments of the present disclosure, a tissue expansion apparatus can be provided that is configured to form a plurality of micro-slits in a layer of tissue to be expanded. For ex vivo meshing of split thickness skin grafts, for example, the apparatus can have a configuration similar to that of a conventional meshing device, except that the cutting surfaces are configured to form micro-slits as described herein that are much shorter than the slit lengths produced by the conventional meshing devices.

Figure 8A:
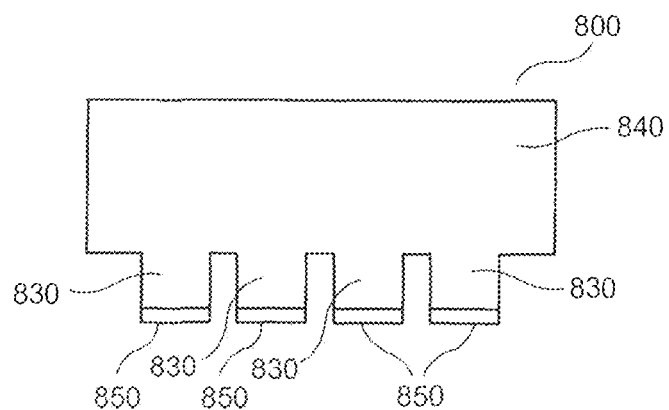
FIG. 8A is an illustration of a first exemplary blade configuration that can be used to form the micro-slits.
Figure 8B:
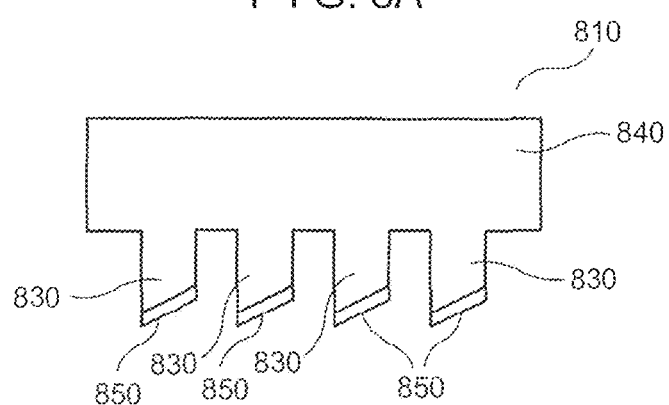
FIG. 8B is an illustration of a second exemplary blade configuration that can be used to form the micro-slits.
Figure 8C:
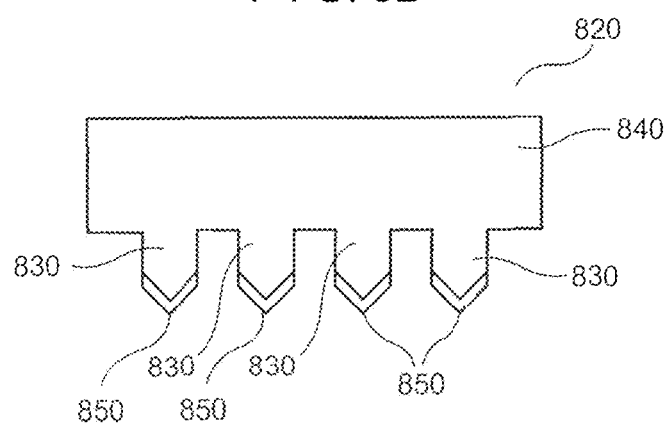
FIG. 8C is an illustration of a third exemplary blade configuration that can be used to form the plurality of micro-slits.

In certain exemplary embodiments, the expansion apparatus can include one or more micro-blades that can be pushed through a skin surface to a desired predetermined depth to form micro-slits. Exemplary micro-blades 800, 810, 820 that can form such micro-slits are shown in FIGS. 8A-8C. The micro-blades 800, 810, 820 can include a plurality of extensions 830 coupled at their proximal ends to a blade body 840. A cutting edge 850 can be provided at a distal end of each extension 830 to facilitate a penetration of the extensions 830 into the tissue to form the micro-slits. For example, the micro-blade 800 can be produced by cutting away portions of a conventional razor blade or the like to form the plurality of extensions 830. Other manufacturing procedures can also be used. The extensions 830 can be very thin and the cutting edge 850 can be very sharp, for example, similar to a razor blade or a scalpel.

The length of the extensions 830 can be approximately the same as the depth of the tissue being expanded. For example, if tissue (such as a half-thickness graft) is being expanded ex vivo, the length of the extensions 830 can be about the same as or greater than the tissue thickness to facilitate the formation of the micro-slits that can pass through the entire thickness of the tissue. The blades 800, 810, 820 can be formed of stainless steel and/or any other suitable material, such as another metal, a polymer, or silicon, and they may optionally be disposable. The approximate depth of the micro-slits formed can correspond to the length of the extensions 830, because the blades 800, 810, 820 can only penetrate the tissue until the lower edge of the blade body 840 contacts the tissue surface. Alternatively or in addition, the extensions 830 that are longer than the desired depth of the micro-slits can be provided. The depth of the micro-slits formed can be controlled, e.g., by providing one or more hilts or stops on the blades 800, 810, 820 located a particular distance above the cutting edge 850 corresponding to the desired micro-slit depth. Such hilt or stop can be fixed to the blades 800, 810, 820, or alternatively it can be adjustable to facilitate the formation of the micro-slits having different depths with a single blade arrangement. The blades 800, 810, 820 can be pressed into the tissue to form a single line of the micro-slits, and this exemplary procedure can be repeated to form an array containing a plurality of such lines of micro-slits, such as the array 100 shown in FIG. 1A.

Figure 9:
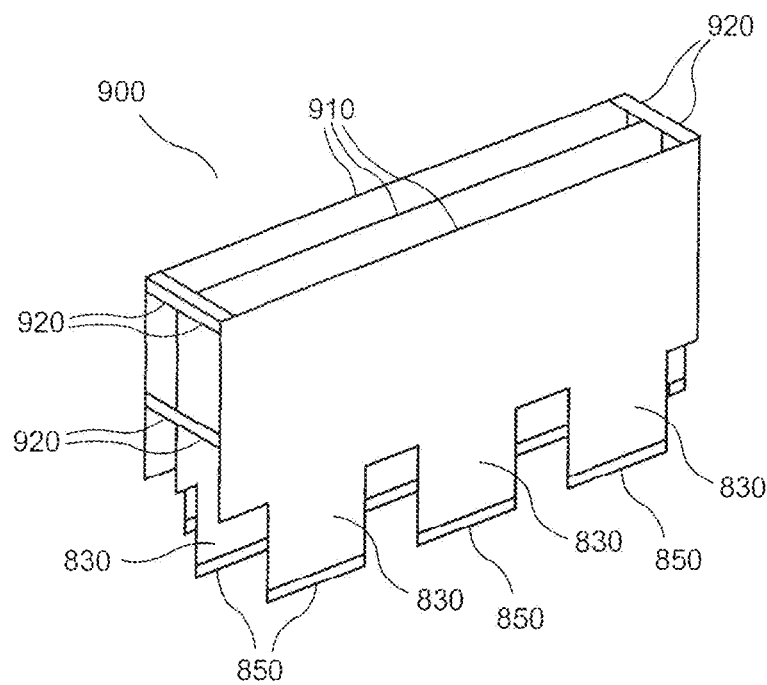
FIG. 9 is an illustration of an exemplary stack of blades that can be used to form a plurality of micro-slits.

According to further exemplary embodiments, an apparatus for forming micro-slits can be provided that includes a stack 900 of blades 910 as shown, e.g., in FIG. 9. The stack 900 of the blades 910 may include a plurality of blades 910 such as those described herein, with spacers 920 provided between the blades 910. The blades 910 can be staggered such that the extensions 830 with cutting edges 850 are configured to create a micro-slit pattern, such as that shown in FIG. 1A or the like, when the lower portion of the stack 900 is pressed into the tissue. The stack 900 of blades 910 can also be pressed onto a particular portion of tissue for a second time, with the blades 910 oriented in a second direction that is substantially orthogonal to a first direction of the blades 910, to produce a pattern of micro-slits, e.g., similar to that shown in FIG. 3.

Figure 10:
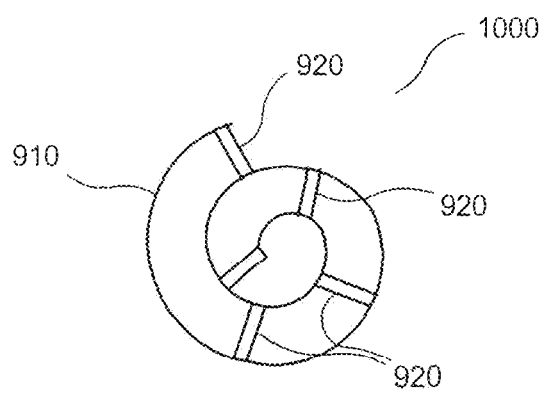
FIG. 10 is an illustration of an exemplary spiral blade configuration that can be used to form the micro-slits.

Other blade configurations can be used to create particular micro-slit patterns. For example, FIG. 10 shows a plan view of a spiral blade 1000 which can be formed by bending the blade 910 into a spiral shape, and which may further include spacers 920 between portions of the spiral. The spiral blade 1000 can be used to form a spiral pattern of micro-slits such as that shown in FIG. 5B. Various micro-slit patterns can be obtained by using different combinations and configurations of blades as described herein.

According to another exemplary embodiment of the present disclosure, an exemplary roller apparatus 1100 (such as that shown in FIG. 11A) can be provided. For example, the roller apparatus 1100 can include a round blade body 1110, with a plurality of substantially coplanar extensions 830 provided around a perimeter of the circular blade body 1110. A cutting edge 850 can be provided on an outer portion of each extension 830, and may optionally extend along a portion or all of the sides of the extensions 830. The blade body 1110 can be configured to rotate around an axle 1140 that can be attached to a handle 1150. The exemplary roller apparatus 1100 can be rolled over a portion of tissue to produce a line of micro-slits. The exemplary roller apparatus 1100 can be used, for example, to easily form a large number of micro-slits over a large area of tissue by rolling the apparatus 1100 across the tissue.

A further exemplary embodiment of a roller apparatus 1120 is shown in FIG. 11B. The exemplary roller apparatus 1120 can include a circular blade body 1110. A plurality of extensions 830 can be provided around the perimeter of the circular blade body 1110, for example, in a staggered configuration. A cutting edge 850 can again be provided on an outer portion of each extension 830, and may optionally extend along to the sides of the extensions 830. The blade body 1110 can be configured to rotate around the axle 1140, which can be attached to a handle 1150. The roller apparatus 1120 can then be rolled over the tissue to produce a plurality of lines of micro-slits at the same time, for example, similar to the array of micro-slits 100 shown in FIG. 1A.

The ease with which an exemplary cutting apparatus can form the micro-slits by cutting through tissue may depend on factors such as, e.g., a sharpness of each cutting edge 850, a width and/or thickness of each extension 830, a rigidity of the tissue, an applied pressure, a number and/or density of the extensions 830, etc. It can be difficult to force a high density of small extensions 830 into the tissue simultaneously. Various modifications to the exemplary embodiments of the apparatus as described herein can be provided to facilitate an easier formation of the micro-slits. For example, the extensions 830 and/or cutting edges 850 can be coated with a lubricant or other low-friction coating. The extensions 830 can be inserted sequentially into the tissue rather than simultaneously, such as with the roller apparatus 1100.

The extensions 830 can also be driven into the tissue using force impulses, e.g., by tapping or hammering using piezoelectric elements, solenoids, pneumatics, hydraulics, etc. In certain embodiments, a vibrating arrangement such as, e.g., a transducer can be mechanically coupled to the apparatus to induce vibrations in the extensions 830 and facilitate their penetration into the tissue. For example, the vibration can be provided at frequencies up to about 100 kHz. Certain advantages of the cutting devices over other techniques for forming slits in the tissue can include disposability, low cost, simplicity, ease of use, and eye-safe operation.

In further exemplary embodiments of the present disclosure, a micro-slit pattern can be formed that includes different parameters (e.g., slit length, orientation, density, etc.) can be provided in different regions of a single portion of tissue. For example, the micro-slit patterns such as those shown in FIG. 1A can be provided at different orientations in different regions of the tissue. The local expansion of the tissue in each region can be utilized in a direction substantially orthogonal to the local micro-slits, as shown in FIG. 1B. Accordingly, a variation in micro-slit parameters in a tissue portion can be used to further accommodate variations in local expansion behavior of the stretched tissue. For example, by varying micro-slit parameters, a particular section of graft tissue can be expanded to better fill a wound area having a shape different than that of the unexpanded graft tissue. Such a variation in micro-slit parameters can also be used to expand tissue in situ to better cover and conform to the shape of an adjacent wound area.

Figure 12A:
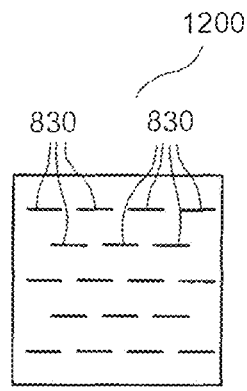
FIG. 12A is an illustration of a first exemplary square pattern of cutting edges that can be used to form the micro-slits in a tissue.
Figure 12B:
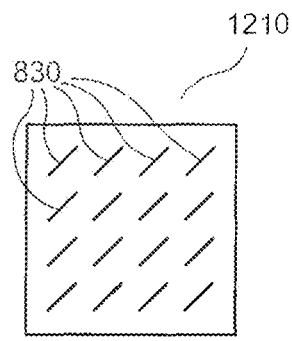
FIG. 12B is an illustration of a second exemplary square pattern of the cutting edges that can be used to form the micro-slits in the tissue.

For example, an exemplary apparatus for facilitating tissue expansion can be provided that includes the extensions 830 arranged in an exemplary array 1200 that has an overall square or rectangular shape, as shown in FIG. 12A. A further exemplary array 1210 that can include the extensions 830 arranged in a diagonal direction is shown in FIG. 12B. For example, such exemplary arrays 1200, 1210 of extensions 830 can be formed using the stack 900 of the blades 910 as shown in FIG. 9. Each extension 830 can include, e.g., a cutting edge 850 provided on a distal portion thereof to facilitate the insertion of the extension 830 into the tissue to form a micro-slit.

Figure 12C:
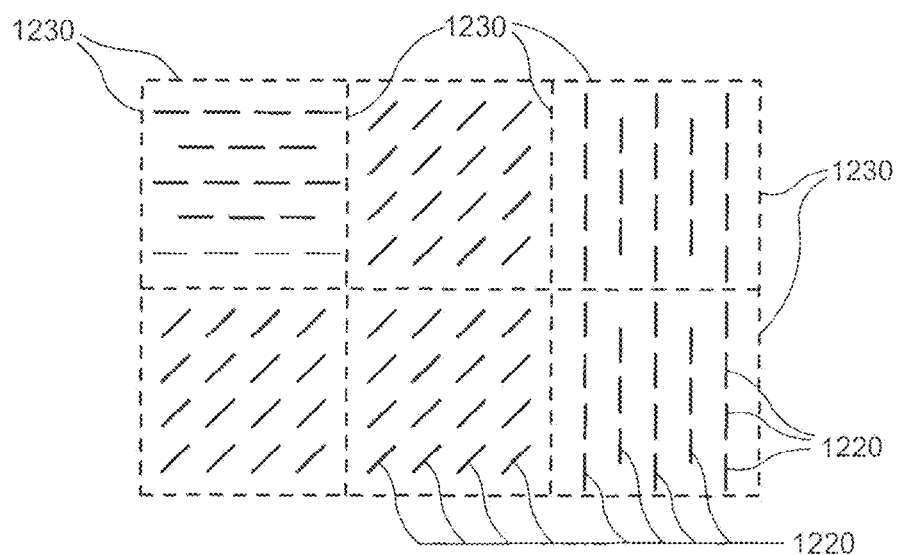
FIG. 12C is an illustration of an exemplary pattern of the micro-slits that can be formed in a tissue using the square patterns of cutting edges shown in FIGS. 12A and 12B.

One or more apparati that includes such an array 1200, 1210 can be pressed into a plurality of regions of the tissue, for example, to form a pattern of the micro-slits such as the exemplary pattern(s) shown in FIG. 12C. The exemplary pattern(s) of micro-slits 1220 shown in FIG. 12C can include several regions outlined by dashed lines 1230, where each region can have a particular local orientation of the micro-slits. The exemplary pattern(s) shown in FIG. 12C can thereby provide a substantially uniform distribution of the micro-slits 1220 over a portion of tissue that includes a variation in local stretching directions (e.g., directions substantially orthogonal to the length of a micro-slit 1220). Providing the arrays 1200, 1210 in a substantially square or rectangular shape, e.g., as shown in FIGS. 12A and 12B, can facilitate the formation patterns of the micro-slits 1220 that are substantially uniformly spaced over a portion of tissue to be stretched.

Figure 13A:
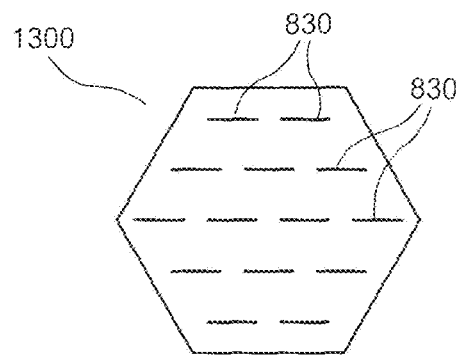
FIG. 13A is an illustration of an exemplary hexagonal pattern of cutting edges that can be used to form the micro-slits in the tissue.

In a further exemplary embodiment, an apparatus for facilitating tissue expansion can be provided that can include a plurality of extensions 830 arranged in an array 1300 that can have an approximately hexagonal shape, as shown in FIG. 13A. As described above with respect to the arrays 1200, 1210 of FIGS. 12A and 12B, the exemplary array 1300 can also be formed, e.g., using the stack 900 of the blades 910 similar to that shown in FIG. 9. The lengths of the blades 910 can be selected to provide the hexagonal array 1300 shown in FIG. 13A.

Figure 13B:
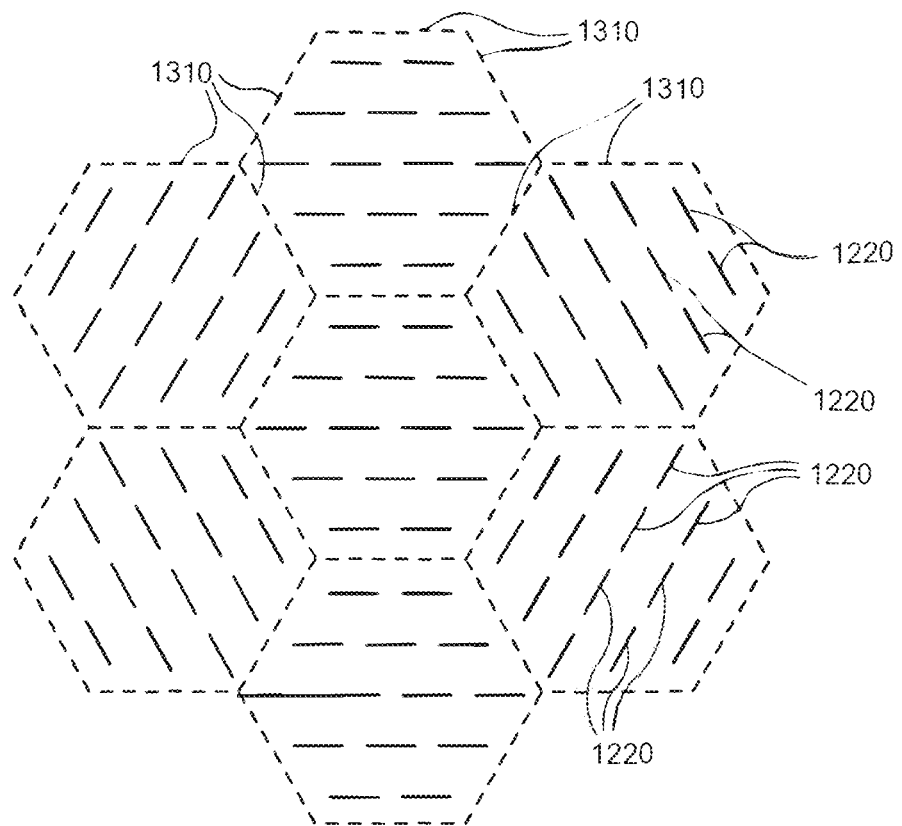
FIG. 13B is an illustration of an exemplary pattern of the micro-slits that can be formed in the tissue using the hexagonal pattern of the cutting edges shown in FIG. 13A.

The apparatus that can include such array 1300 can be pressed into a plurality of regions of a tissue, for example, to form a pattern of micro-slits 1220 that can cover a portion of tissue to be stretched with a substantially uniform density of such micro-slits. For example, the exemplary pattern of micro-slits 1220 shown in FIG. 13B can include several regions outlined by dashed lines 1310, where the micro-slits 1220 in each region can be formed by pressing the array 1300 of the extensions 830 into the tissue, and withdrawing it. The exemplary pattern shown in FIG. 13B can be used to facilitate stretching of tissue (e.g., skin) over a rounded surface (e.g., an elbow, a chin, or the like), similar to the circular pattern shown in FIG. 5A. Other uniform distributions of the micro-slits 1220 having variations in local preferred stretching directions can also be formed using the apparatus that can include the exemplary array 1300 of the extensions 830 shown in FIG. 13A.

In a further exemplary embodiment, an apparatus that includes an array of the extensions 830 can be provided, e.g., in a form of a triangle or another geometric shape, to facilitate formation of a pattern of the micro-slits 1220 that can have various local orientations thereof, and which can be used to provide a substantially uniform density or distribution of the micro-slits 1220 over a portion of the tissue as described above.

Figure 14:
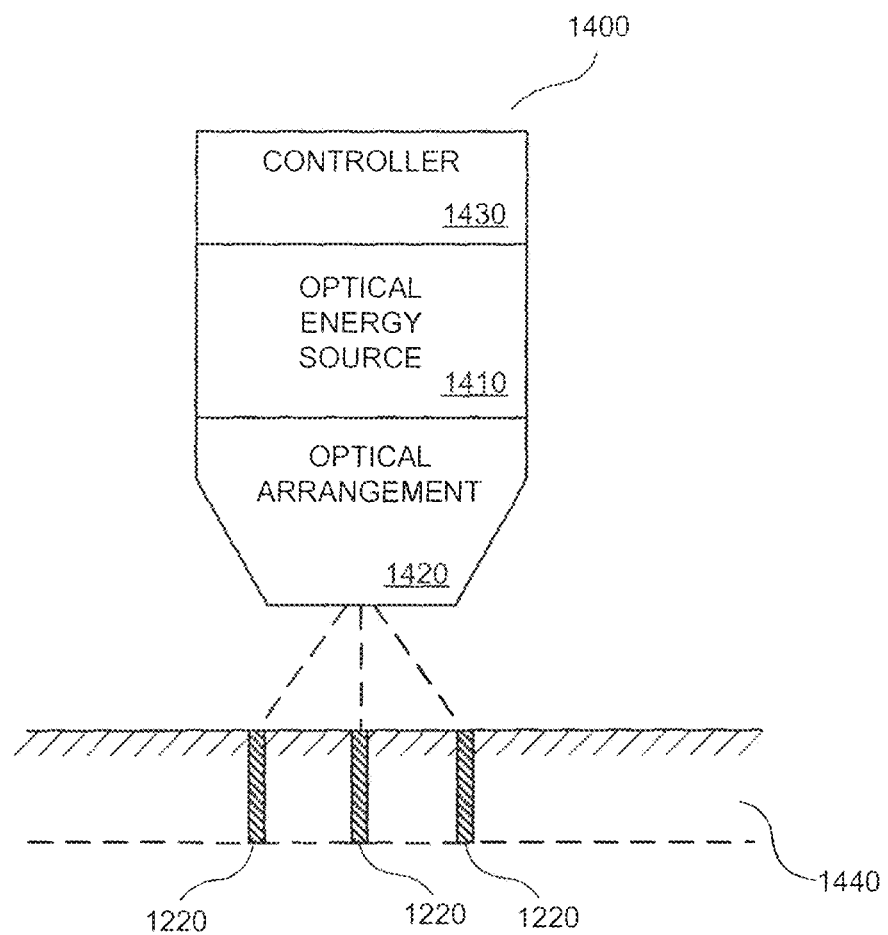
FIG. 14 is a schematic illustration of an exemplary laser apparatus that can be used to form the micro-slits in accordance with exemplary embodiments of the present disclosure.

In still another exemplary embodiment, an optical apparatus 1400 as shown in FIG. 14 can be used to form a plurality of micro-slits as described herein. The exemplary optical apparatus 1400 can include an optical energy source 1410, an optical arrangement 1420, and a control arrangement 1430. The optical energy source 1410 can be, e.g., an ablative laser that is configured to produce minimal thermal injury, such as a pulsed $CO_2$ laser, an Erbium (Er) laser, an excimer laser, or any one of various conventional femtosecond lasers. Other sources of optical energy that are configured to ablate or cut thin regions of the tissue can also be used.

For example, pulsed $CO_2$ lasers and pulsed Er lasers that are commonly used in dermatology and plastic surgery for tissue removal can generate a residual thermal damage layer in tissue next to an ablated region that can be between about 50 and about 200 micrometers in thickness. Excimer lasers, including a 193 nm excimer laser, can also be used and are capable of cutting tissue with almost no observable residual thermal damage. Such lasers are commonly used for LASIK procedures in corneal tissue. Femtosecond lasers, for example, having a pulse energy of greater than about 1 microjoule, when focused appropriately, can also sever or ablate tissue while generating a negligible amount of thermal damage in adjacent tissue. Such ablative lasers can operate at wavelengths and/or power densities for which the tissue exhibits strong optical absorption. Exemplary advantages of using optical energy, e.g., a laser, to form micro-slits in tissue as compared with blades or other material cutting devices can include speed, precision, depth control, arbitrary micro-slit pattern design, sterility, and non-contact operation.

The optical arrangement 1420 can include one or more waveguides, beam splitters, and/or mirrors, and can be configured to direct energy from the optical energy source 1410 towards the tissue layer 1440 to form a plurality of the micro-slits 1220 therein. The control arrangement 1430 can be configured to adjust parameters of the optical energy source 1410 and the optical arrangement 1420 to affect and/or determine a position, length, and depth of the micro-slits 1220. The exemplary optical apparatus 1400 can be provided in a fixed position relative to the tissue layer 1440. Alternatively, at least a portion of the optical apparatus 1400 can be provided in or as a handpiece or the like, which can be translated or moved over the tissue layer 1440 to create larger regions of the micro-slits 1220.

EXAMPLE

Figure 15A:
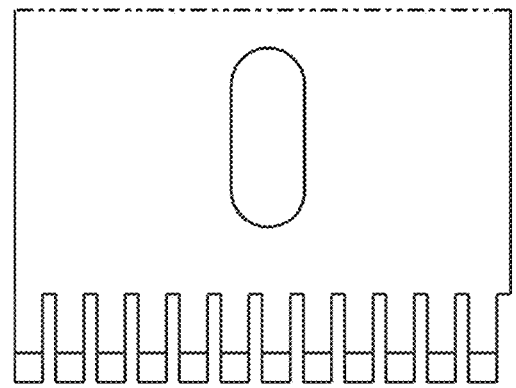
FIG. 15A is an image of an exemplary blade that can be used to form the micro-slits.
Figure 15B:
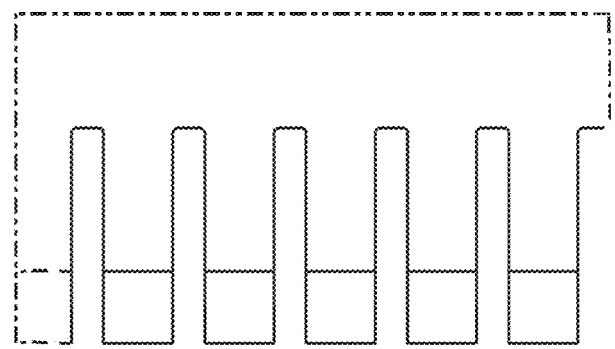
FIG. 15B is a further image of the exemplary blade shown in FIG. 15A.

Images of an exemplary blade in accordance with embodiments of the present disclosure are shown in FIGS. 15A and 15B. The exemplary blade illustrated in FIG. 15A can be similar to the exemplary blade 800 illustrated in FIG. 8A. A close-up view of the extensions provided on the blade 800, each with a cutting edge at a distal end thereof, is shown in FIG. 15B.

Figure 16A:
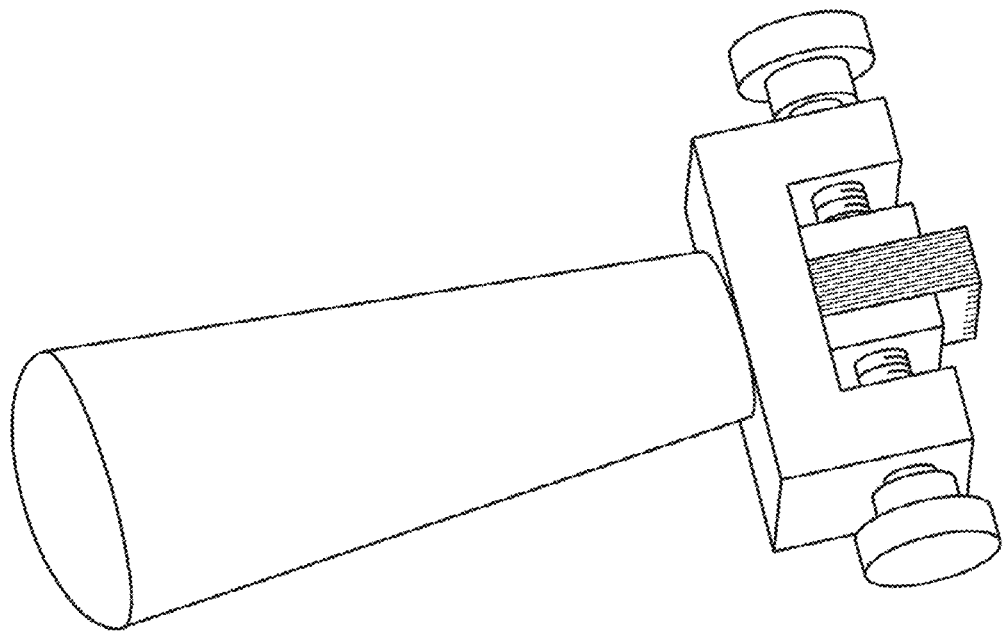
FIG. 16A is a first image of an exemplary apparatus that can be used to form the micro-slits to facilitate tissue stretching in accordance with embodiments of the present disclosure.
Figure 16B:
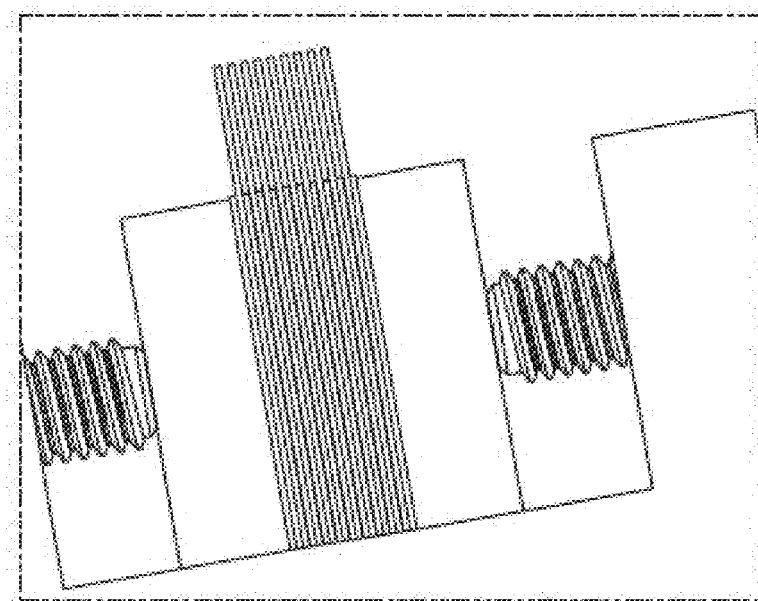
FIG. 16B is a second image of a portion of the apparatus shown in FIG. 16A.
Figure 16C:
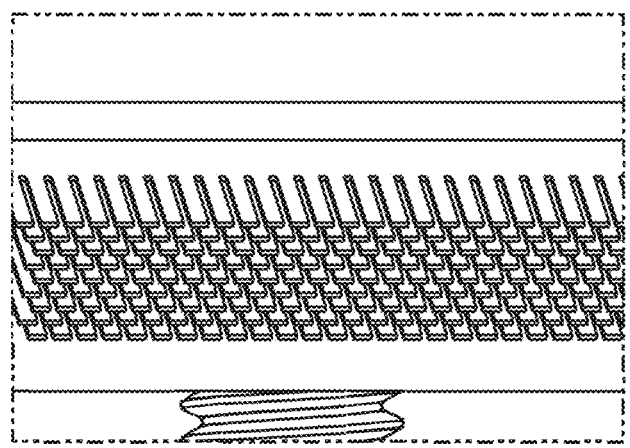
FIG. 16C is a third image of a portion of the apparatus shown in FIG. 16A.
Figure 16D:
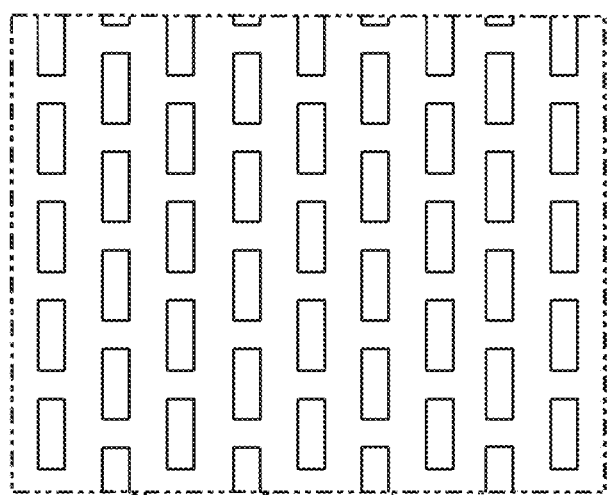
FIG. 16D is a fourth image of a portion of the apparatus shown in FIG. 16A, showing the pattern of the cutting edges.

Images of the exemplary apparatus in accordance with certain exemplary embodiments of the present disclosure are shown in FIGS. 16A-16D. The exemplary apparatus shown in FIG. 16A can include a handle attached to plurality of blades, where each blade is similar to the blade shown in FIG. 15A. FIGS. 16B and 16C are close-up images of the stack of blades having spacers between them, similar to the stack of the blades 900 shown in FIG. 9. FIG. 16D provides an image of the array of cutting edges provided by the exemplary apparatus, which can be used to form a pattern of micro-slits that is similar, e.g., to the pattern of the micro-slits shown in FIG. 1A.

Figure 17A:
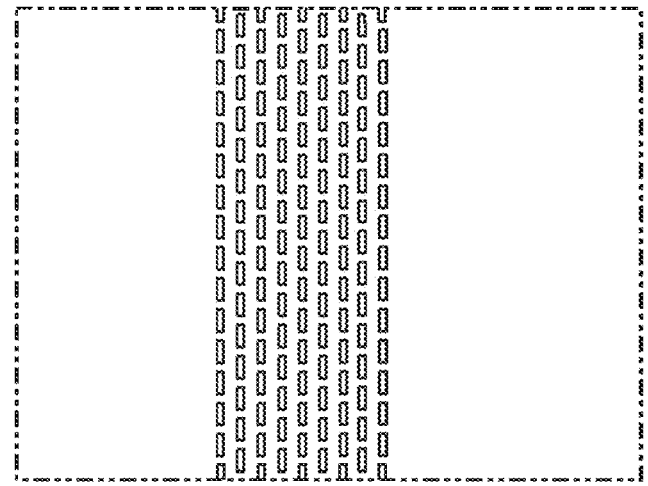
FIG. 17A is an image of a piece of graft skin tissue that includes the micro-slits provided therein in accordance with the exemplary embodiments of the present disclosure.

A piece of human graft skin tissue is shown in FIG. 17A. A portion of this tissue can include a pattern of micro-slits formed therein using the exemplary apparatus shown in FIGS. 16A-16D, in accordance with the exemplary embodiments of the present disclosure. The pattern of micro-slits can be similar to the exemplary pattern shown in FIG. 1A.

Figure 17B:
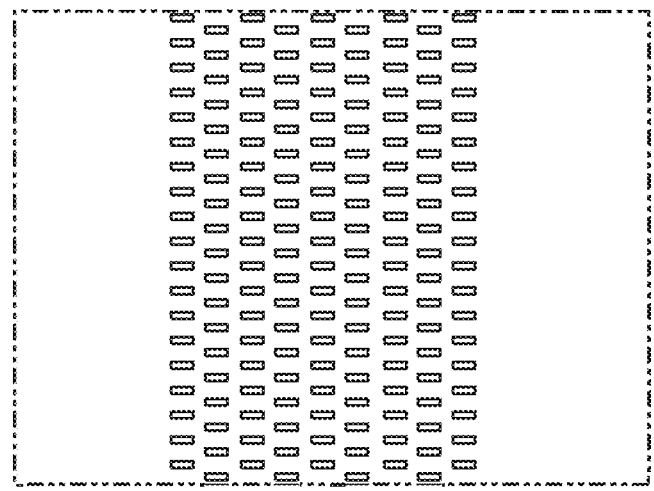
FIG. 17B is an image of the piece of the graft skin tissue shown in FIG. 17A after such skin tissue has been stretched.

FIG. 17B illustrates an image of the skin tissue shown in FIG. 17A after it has been stretched sideways. Each micro-slit can be widened to form a small gap, and the portion of tissue that includes the pattern of micro-slits appears to have expanded substantially uniformly in a left-right direction. This stretched pattern of gaps is similar to that shown in FIG. 1B. A maximum dimension of each gap is small, e.g., on the order of about a millimeter or less as described herein. Accordingly, the graft tissue may regrow to rapidly fill in these small gaps, e.g., when the graft tissue is applied to a recipient site, and the healed graft tissue may appear substantially normal because of the small size scale of the plurality of healed gaps.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents, patent applications, and other publications cited herein are incorporated herein by reference in their entireties.

What is claimed is:

1. An apparatus for forming micro-slits in a tissue, the apparatus comprising:
    a roller apparatus including a cylindrical body;
    a first extension and a second extension protruding from the cylindrical body, wherein, when the apparatus is rolled over the tissue, the first extension penetrates the tissue and generates a first micro-slits in the tissue, and the second extension can penetrate the tissue and generate a second micro-slit;
    wherein each of the first micro-slit and the second micro-slit has a depth of less than about 0.6 mm in skin tissue, or less than about one third of a total skin thickness.

2. The apparatus of claim 1, further including a handle and an axle attached to the handle, wherein the cylindrical body is configured to rotate about the axle.

3. The apparatus of claim 1, wherein the first extension is coated with a lubricant or a low-friction coating.

4. The apparatus of claim 1, wherein the first extension and the second extension are spaced apart along a circumference of the cylindrical body, so that the first micro-slit and the second micro-slit are generated sequentially.

5. The apparatus of claim 1, wherein the first extension and the second extension are spaced apart along an axial direction of the cylindrical body.

6. The apparatus of claim 1, wherein each of the first extension and the second extension comprise a microcutting blade.

7. The apparatus of claim 1, further comprising a transducer configured to induce vibration of the first and second extensions.

8. An apparatus for forming micro-slits in a tissue, the apparatus comprising:
    a roller apparatus including a cylindrical body; and
    a first extension protruding from the cylindrical body, wherein, when the apparatus is rolled over the tissue, the first extension can penetrate the tissue and generate a first micro-slit in the tissue;
    wherein the first micro-slit has a depth of less than about 0.6 mm in skin tissue, or less than about one third of a total skin thickness.

9. The apparatus of claim 8, further including a handle and an axle attached to the handle, wherein the cylindrical body is configured to rotate about the axle.

10. The apparatus of claim 8, wherein the first extension is coated with a lubricant or a low-friction coating.

11. The apparatus of claim 8, wherein the first extension comprises a microcutting blade.

12. The apparatus of claim 8, further comprising a transducer configured to induce vibration of the first extension.

13. The apparatus of claim 8, wherein the first extension is one of a first plurality of extensions, each extension of the first plurality of extensions configured to penetrate the tissue and generate a corresponding micro-slit sequentially with another extension of the first plurality of extensions, wherein the micro-slits generated by the first plurality of extensions comprise a line of micro-slits.

14. The apparatus of claim 8, further comprising a second extension protruding from the cylindrical body, wherein, when the apparatus is rolled over the tissue, the second extension can penetrate the tissue and generate a second micro-slit in the tissue.

15. The apparatus of claim 14, wherein the second extension is spaced apart from the first extension in an axial direction of the cylindrical body.

16. An apparatus for forming micro-slits in a tissue, the apparatus comprising:
    a roller apparatus coupled to an axle; and
    a plurality of extensions protruding from the roller apparatus so that, when the roller apparatus is rolled over the tissue, the plurality of extensions penetrate the tissue and simultaneously generate a plurality of micro-slits in the tissue;
    each of the plurality of extensions having a width that is approximately a length of a micro-slit formed within the tissue by the respective extension and a depth of less than about one-third of a total skin thickness.

17. The apparatus of claim 16, wherein the plurality of extensions are circumferentially spaced apart around the roller apparatus.

18. The apparatus of claim 16, wherein the plurality of extensions are provided in a pattern on the roller apparatus configured to generate a pattern of micro-slits in the tissue facilitating multidirectional tissue expansion.

19. The apparatus of claim 16, wherein the plurality of extensions are configured to form the micro-slits having a depth of less than about 0.6 mm.

20. The apparatus of claim 16, wherein the width of at least one of the plurality of extensions is configured to:
- form a micro-slit with a length of about 2 mm or smaller; or
- form a micro-slit with a length of about 0.8 mm or smaller.

\* \* \* \* \*